United States Patent
Gross (10) Patent No.: US 10,524,736 B2
(45) Date of Patent: Jan. 7, 2020

(54) SYSTEM AND METHOD TO DETECT SIGNIFICANT ARRHYTHMIC EVENTS THROUGH A PHOTOPLETHYSMOGRAM (PPG) AND ACCELEROMETER

(71) Applicant: KONINKLIJKE PHILIPS N.V., Eindhoven (NL)

(72) Inventor: Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 571 days.

(21) Appl. No.: 14/648,724

(22) PCT Filed: Dec. 6, 2013

(86) PCT No.: PCT/IB2013/060707
§ 371 (c)(1),
(2) Date: Jun. 1, 2015

(87) PCT Pub. No.: WO2014/091382
PCT Pub. Date: Jun. 19, 2014

(65) Prior Publication Data
US 2015/0305684 A1    Oct. 29, 2015

Related U.S. Application Data

(60) Provisional application No. 61/737,410, filed on Dec. 14, 2012.

(51) Int. Cl.
*A61B 5/00* (2006.01)
*A61B 5/11* (2006.01)
(Continued)

(52) U.S. Cl.
CPC .......... *A61B 5/7246* (2013.01); *A61B 5/0205* (2013.01); *A61B 5/1102* (2013.01);
(Continued)

(58) Field of Classification Search
CPC . A61B 5/7246; A61B 5/0205; A61B 5/02416; A61B 5/1102; A61B 5/1118;
(Continued)

(56) References Cited

U.S. PATENT DOCUMENTS 7,468,032 B2    12/2008  Stahmann
7,794,406 B2 *  9/2010   Reisfeld ............... A61B 5/0402
                                                         600/479
(Continued)

FOREIGN PATENT DOCUMENTS

EP         1908401 A1     4/2008
JP        2011210844     10/2011
(Continued)

OTHER PUBLICATIONS

Johansson, A.; Neural network for photoplethysmographic respiratory rate monitoring; 2003; Medical & Biological Engineering & Computing; 41(3)242-248.
(Continued)

*Primary Examiner* — Carl H Layno
*Assistant Examiner* — Dacheng Xie (57) ABSTRACT

The medical system and method detect arrhythmic events. The medical system includes at least one processor programmed to perform the method. A photoplethysmogram (PPG) signal generated using a PPG probe positioned on or within a patient and a pulse signal generated using an accelerometer positioned on or within the patient received. Features from the PPG signal are extracted to PPG feature vectors, and features are extracted from the pulse signal to pulse feature vectors. The PPG feature vectors are correlated with the pulse feature vectors, and correlated PPG feature vectors and correlated pulse feature vectors are evaluated to detect arrhythmic events.

21 Claims, 3 Drawing Sheets

(51) Int. Cl.
*A61B 5/113* (2006.01)
*A61B 5/0205* (2006.01)
*A61B 5/024* (2006.01)
*A61B 5/08* (2006.01)

(52) U.S. Cl.
CPC ............. *A61B 5/113* (2013.01); *A61B 5/1118* (2013.01); *A61B 5/7221* (2013.01); *A61B 5/7278* (2013.01); *A61B 5/7282* (2013.01); *A61B 5/02427* (2013.01); *A61B 5/08* (2013.01); *A61B 2562/0219* (2013.01)

(58) Field of Classification Search
CPC ..... A61B 5/113; A61B 5/7221; A61B 5/7278; A61B 5/7282; A61B 5/00; A61N 1/36542; A61N 1/36573; G06F 19/30
USPC .................................................. 600/300–301
See application file for complete search history.

(56) References Cited

U.S. PATENT DOCUMENTS

| | | | |
|---|---|---|---|
| 8,032,206 B1* | 10/2011 | Farazi | A61B 5/0205 600/509 |
| 8,821,418 B2 | 9/2014 | Meger | |
| 8,878,677 B2 | 11/2014 | Nielsen | |
| 2003/0212336 A1* | 11/2003 | Lee | A61B 5/02416 600/504 |
| 2004/0002637 A1* | 1/2004 | Huang | A61B 5/14551 600/300 |
| 2006/0084879 A1* | 4/2006 | Nazarian | A61B 5/02438 600/500 |
| 2007/0149890 A1* | 6/2007 | Li | A61B 5/0464 600/515 |
| 2008/0200775 A1* | 8/2008 | Lynn | A61B 5/02028 600/301 |
| 2008/0275520 A1* | 11/2008 | Hopper | A61N 1/368 607/17 |
| 2008/0275526 A1* | 11/2008 | Lozano | A61N 1/36082 607/45 |
| 2010/0145201 A1* | 6/2010 | Westbrook | A61B 5/0205 600/484 |
| 2010/0298899 A1* | 11/2010 | Donnelly | A61B 5/02055 607/6 |
| 2011/0046498 A1* | 2/2011 | Klap | A61B 5/0205 600/534 |
| 2011/0106195 A1* | 5/2011 | Kornet | A61B 5/02 607/14 |
| 2011/0270048 A1* | 11/2011 | Addison | A61B 5/02416 600/301 |
| 2012/0030290 A1 | 2/2012 | Yin | |
| 2012/0203077 A1 | 8/2012 | He et al. | |
| 2012/0262303 A1* | 10/2012 | Fahey | A61B 5/0006 340/870.02 |
| 2013/0080808 A1* | 3/2013 | Verma | G06F 19/3412 713/322 |

FOREIGN PATENT DOCUMENTS

| | | | |
|---|---|---|---|
| WO | WO 2010095064 A1 * | 8/2010 | .......... A61B 5/0002 |
| WO | 2010108287 A1 | 9/2010 | |
| WO | 2012103296 A2 | 8/2012 | |

OTHER PUBLICATIONS

Spigulis, J., et al.; Wearable wireless photoplethysmography sensors; 2008; Proc. of SPIE; vol. 6991; pp. 699120-699120-7.

* cited by examiner

SYSTEM AND METHOD TO DETECT SIGNIFICANT ARRHYTHMIC EVENTS THROUGH A PHOTOPLETHYSMOGRAM (PPG) AND ACCELEROMETER

CROSS REFERENCE TO RELATED APPLICATIONS

This application is a national filing of PCT application Serial No. PCT/IB2013/060707, filed Dec. 6, 2013, published as WO 2014/091382 A1 on Jun. 19, 2014, which claims the benefit of U.S. provisional application Ser. No. 61/737,410 filed Dec. 14, 2012, which is incorporated herein by reference.

The present application relates generally to patient monitoring. It finds particular application in conjunction with reducing false alarms and will be described with particular reference thereto. However, it is to be understood that it also finds application in other usage scenarios and is not necessarily limited to the aforementioned application.

Electrocardiograph (ECG) monitoring for cardiac events, such as ischemia and arrhythmic events, is important for detecting patient deterioration. Arrhythmic events of interest include, for example, onset and end of Atrial Fibrillation or Flutter (A-Fib), Ventricular Tachycardia (V-Tach), Ventricular Fibrillation (V-Fib), and Asystole. However, ECG monitoring poses a number of challenges.

Conventional ECG technologies are cumbersome, laborious with regards to maintaining signal acquisition, and costly. In many cases, continuous ECG requires significant work of clinicians to maintain proper electrode and lead contact to the skin. Failure to do so can result in false detection of cardiac events and false alarms, or clinically action-less events. Further, even with the development of smaller, lower cost, and wearable technologies, many of these challenges are still present.

The present application provides new and improved methods and systems which overcome the above-referenced problems and others.

In accordance with one aspect, a medical system for detecting arrhythmic events is provided. The system includes at least one processor programmed to receive a photoplethysmogram (PPG) signal generated using a PPG probe positioned on or within a patient and receive a pulse signal generated using an accelerometer positioned on or within the patient. Further, the at least one processor is programmed to extract features from the PPG signal to PPG feature vectors, extract features from the pulse signal to pulse feature vectors, correlate the PPG feature vectors with the pulse feature vectors, and evaluate correlated PPG feature vectors and correlated pulse feature vectors to detect arrhythmic events.

In accordance with another aspect, a medical method for detecting arrhythmic events is provided. A PPG signal generated using a PPG probe is positioned on or within a patient and a pulse signal generated using an accelerometer positioned on or within the patient are received. Features are extracted from the PPG signal to PPG feature vectors, and features are extracted from the pulse signal to pulse feature vectors. The PPG feature vectors are correlated with the pulse feature vectors, and correlated PPG feature vectors and correlated pulse feature vectors are evaluated to detect arrhythmic events.

In accordance with another aspect, a medical system for detecting arrhythmic events is provided. The system includes a first feature extraction unit extracting features from a PPG signal to PPG feature vectors. The PPG signal is generated using a PPG probe positioned on or within a patient. The system further includes a second feature extraction unit extracting features from a pulse signal and a respiration signal to pulse feature vectors and respiration feature vectors, respectively. The pulse and respiration signals are generated using an accelerometer positioned on or within the patient. The system further includes an arrhythmia unit configured to correlate the PPG feature vectors with the pulse and respiration feature vectors and evaluate correlated PPG feature vectors and correlated pulse and respiration feature vectors to detect arrhythmic events.

One advantage resides in more reliable detection of arrhythmic events.

Another advantage is in detecting arrhythmic events without the need for electrocardiograph (ECG) monitoring.

Another advantage resides in the ability to detect arrhythmic events periodically without the need for continuous monitoring.

Still further advantages of the present invention will be appreciated to those of ordinary skill in the art upon reading and understand the following detailed description including detection of other physiologic conditions that warrant notification to the patient's care provider or suitable responder to the detected condition.

The invention may take form in various components and arrangements of components, and in various steps and arrangements of steps. The drawings are only for purposes of illustrating the preferred embodiments and are not to be construed as limiting the invention.

The present invention proposes to detect arrhythmic events by use of a photoplethysmogram (PPG) signal and respiration and pulse signals, the respiration and pulse signals being determined from an accelerometer. These events can be detected with high confidence by cross correlation of the accelerometer based respiration and pulse signals with the PPG signal. Further, detected events can be used to generate alerts to clinicians with high confidence.

Figure 1:
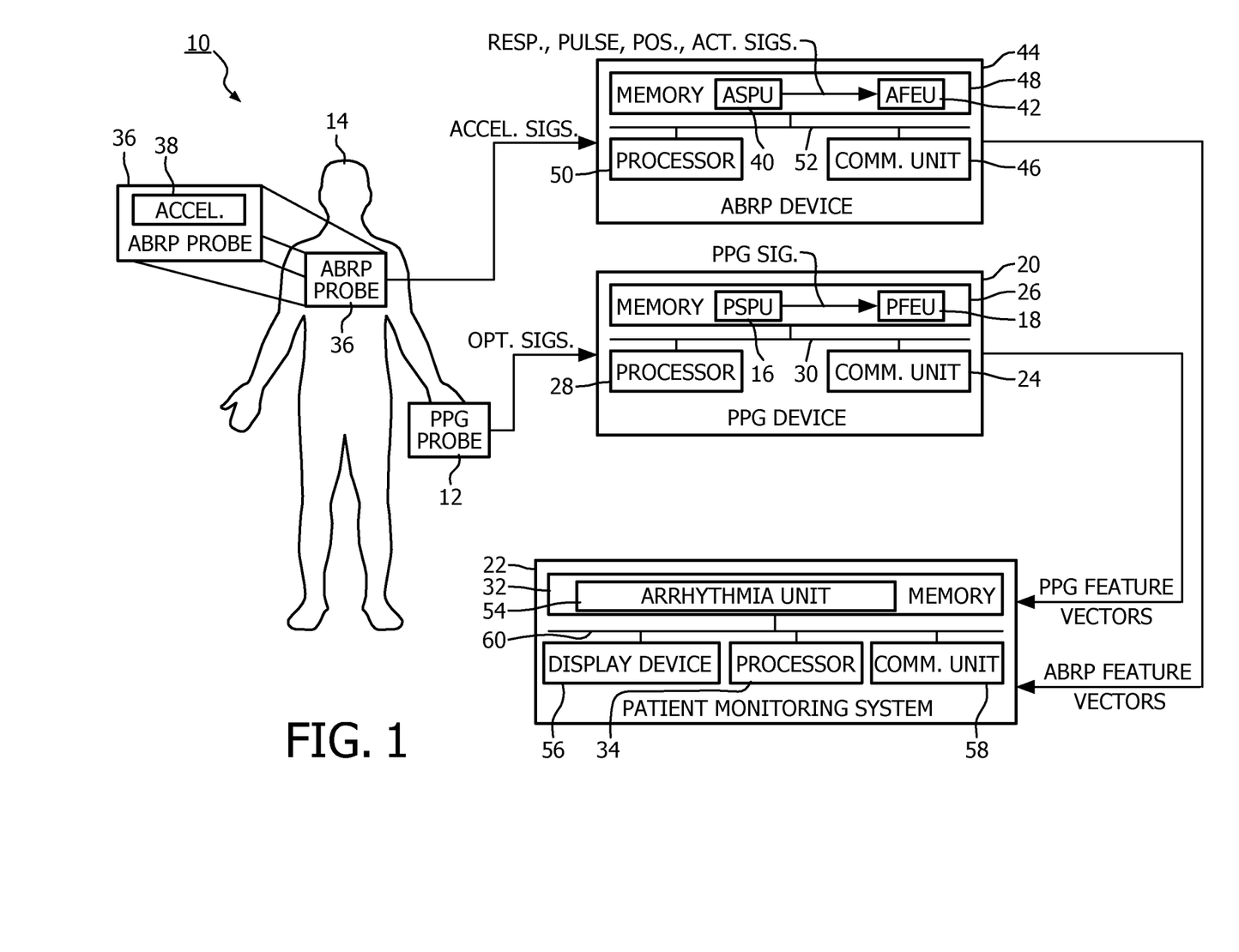
FIG. 1 illustrates one embodiment of a medical system for detecting arrhythmic events.
Figure 2:
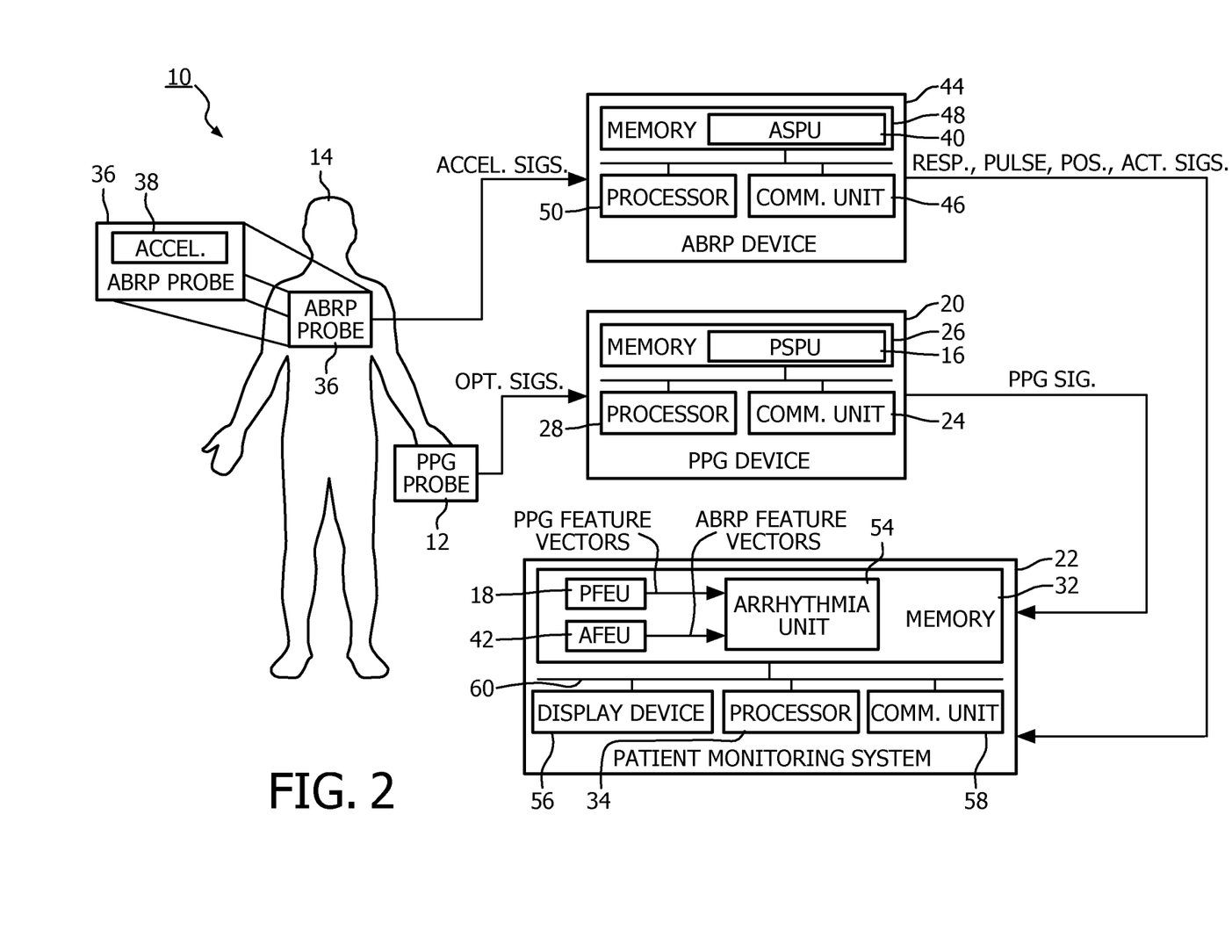
FIG. 2 illustrates another embodiment of a medical system for detecting arrhythmic events.

With reference to FIGS. 1 and 2, a medical system 10 includes a PPG probe 12 facilitating the generation of a PPG signal and/or other signals. Typically, the PPG signal is generated using pulse oximetry, but other approaches for generating the PPG signal are contemplated. The PPG probe 12 is placed on or within an associated patient 14.

When pulse oximetry is employed to generate the PPG signal, the PPG probe 12 is placed on or around a thin part of the patient 14. In the case of an infant, the PPG probe 12 is usually placed across a foot. Otherwise, the PPG probe 12 is usually placed across a fingertip, across an earlobe, in the web between the index finger and thumb (princeps pollicis artery), or on the forehead. Further, when pulse oximetry is employed, the PPG probe 12 includes one or more light sources which are controlled to pass light at red (e.g., around 660 nm) and infrared (e.g., around 940 nm) wavelengths sequentially through the patient 14 to a photo-detector of the PPG probe 12. The changing absorbance at each of the two wavelengths is measured by the photo-detector to create an optical signal.

A PPG signal processing unit (PSPU) 16 processes one or more signals generated by the PPG probe 12 (e.g., the optical signal) to generate the PPG signal and/or the other signals. Suitably, the PPG signal and/or the other signals are continuous.

Further, a PPG feature extraction unit (PFEU) 18 processes the PPG signal to extract one or more features to PPG feature vectors. Features that can be extracted include signal quality index (SQI) for the PPG signal, signal stability of the PPG signal, pulse references (i.e., detected pulse identifiers (IDs)) for a last n pulses (e.g., n=4 or 8), inter pulse intervals (IPIs) for the pairs of adjacent pulses of the last n pulses, median IPI for the last n pulses, and inop messaging. A pulse reference for a pulse can, for example, be a master clock index. Typically, all of these features are extracted to a PPG feature vector.

The PFEU 18 typically only extracts the features to a PPG feature vector when the SQI of the PPG signal exceeds a predetermined threshold. The predetermined threshold is set at a level where a user of the medical system 10 deems the signal quality sufficiently high to reliably extract the features. Further, the PFEU 18 typically only extracts the features according to a predetermined sampling rate, such as, for example, 10 milliseconds. The predetermined sampling rate can be set by a user of the medical system 10 based upon the computational resources (e.g., processing power and memory) of the medical system 10 and/or the granularity of PPG feature vectors needed to reliably monitor patients.

The PSPU 16 and the PFEU 18 can each be software (i.e., processor executable instructions), hardware, or a combination of the two. When the PSPU 16 or the PFEU 18 is, or includes, software, the software is stored on one or more program memories and executed by one or more processors.

A PPG device 20 is positioned proximate to the patient 14, typically at the patient's bedside or in a self-contained device. Further, the PPG device is typically worn by the patient 14. Further, the PPG device 20 can be integrated with the PPG probe 12. The PPG device 20 controls the PPG probe 12 and receives the signals generated by the PPG probe 12. The PPG device 20 includes the PSPU 16 and typically the PFEU 18. However, the PFEU 18 can be remote from the PPG device 20, for example, within a patient monitoring system (PMS) or data aggregator.

Using the PSPU 16, the PPG device 20 processes the signals to generate the PPG signal. Where the PPG device 20 includes the PFEU 18, the PPG device 20 uses the PFEU 18 to process the PPG signal and generate the PPG feature vectors. The PPG feature vectors are then relayed to a PMS 22 as they are generated using a communication unit 24 of the PPG device 20. Where the PPG device 20 does not include the PFEU 18, the PPG device 20 relays the PPG signal to the PFEU 18 using the communication unit 24. Alternately the raw PPG signal can be sent to the PMS 22 where the signal extraction can be accomplished on the reconstruction of the waveform.

One or more program memories 26 of the PPG device 20 store any software of the PSPU 16 and/or the PFEU 18. Further, one or more processors 28 of the PPG device 20 execute the software on the program memories 26. One or more system buses 30 interconnect the components of the PPG device 20, such as the processors 28, the program memories 26 and the communication unit 24.

As illustrated in FIG. 1, both the PSPU 16 and the PFEU 18 are software stored on the program memories 26 of the PPG device 20, where the processors 28 of the PPG device 20 execute the software. As illustrated in FIG. 2, both the PSPU 16 and the PFEU 18 are software. The PSPU 16 is stored on the program memories 26 of the PPG device 20, where the processors 28 of the PPG device 20 execute the software. Further, the PFEU 18 is stored on one or more program memories 32 of the PMS 22, where one or more processors 34 of the PMS 22 execute the software.

An acceleration based respiration and pulse (ABRP) probe 36 is positioned on or within the patient 14, typically proximate to the heart (e.g., within the thorax) or the anterior costal cartilage. Further, the ABRP probe 36 can be integrated with, positioned on, or positioned proximate to the PPG probe 12. The ABRP probe 36 includes an accelerometer 38. Typically, the accelerometer 38 is a three-dimensional (3D) or 3-axis accelerometer. However, the accelerometer 38 can measure acceleration in less than three dimensions. The accelerometer 38 generates one or more accelerometer signals indicative of acceleration. Typically, the accelerometer signals include an accelerometer signal for each dimension of the accelerometer 38.

An ABRP signal processing unit (ASPU) 40 processes the acceleration signals to generate pulse, respiration, position and activity signals from the acceleration signals. Other signals can also be generated from the acceleration signals, such as a ballistocardiograph (BCG) signal or a heart rate signal. The position signal indicates changes in positioning of the ABRP probe 36 over time, and the activity signal indicates the activity level of the patient 14. The activity level can, for example, be determined through analysis of change in position over a last predetermined period of time. Suitably, the signals are continuous or intermittent with the periodicity in concordance with the PPG periodicity.

Further, an ABRP feature extraction unit (AFEU) 42, for each of the pulse, respiration, position and activity signals, processes the signal to extract one or more features to ABRP feature vectors. An ABRP feature vector can be an ABRP pulse feature vector, an ABRP respiration feature vector, an ABRP position feature vectors or an ABRP activity feature vectors depending upon the signal from which the features were extracted. ABRP pulse feature vectors are created together with ABRP respiration feature vectors. Hence, when an ABRP pulse feature vector is created, an ABRP pulse feature vector is created for the same time window. Similarly, ABRP position feature vectors are created together with ABRP activity feature vectors.

Features that can be extracted for the pulse signal include SQI of the pulse signal, pulse references (i.e., detected pulse IDs) for a last n pulses (e.g., n=4 or 8), inter pulse intervals (IPIs) for the pairs of adjacent pulses of the last n pulses, median IPI for the last n pulses, and inop messaging. A pulse reference for a pulse can, for example, be a master clock index. Features that can be extracted for the respiration signal include SQI of the respiration signal, respiration references (i.e., detected respiration IDs) for a last n breaths (e.g., n=4 or 8), inter breath intervals (IBI) for the pairs of adjacent breaths of the last n breaths, median IBI for the last n breaths, and inop messaging. A respiration reference for a breath can, for example, be a master clock index. Features that can be extracted for the position signal include position, position history (e.g., position over the last predetermined amount of time), and end user messaging interface. Features that can be extracted for the activity signal include activity level, activity level history (e.g., activity over the last predetermined amount of time), and end user messaging interface. Typically, all of the above enumerated features for all the signals are extracted.

The AFEU 42 only extracts features to an ABRP feature vector when the SQI of the corresponding signal exceeds a predetermined threshold. The predetermined threshold is set at a level where a user of the medical system deems the signal quality sufficiently high to reliable extract the features. An ABRP pulse feature vector is created only when both the SQI for the pulse signal exceeds the corresponding predetermined threshold and the SQI for the respiration signal exceeds the corresponding predetermined threshold. The same applies to an ABRP respiration feature vector. Similarly, an ABRP position feature vector is created only when both the SQI for the position signal exceeds the corresponding predetermined threshold and the SQI for the activity signal exceeds the corresponding predetermined threshold. The same applies to an ABRP activity pulse feature vector.

Further, the AFEU 42 typically only extracts features from a signal according to a predetermined sampling rate, such as, for example, 10 milliseconds. The predetermined sampling rate can be set by a user of the medical system 10 based upon the computational resources (e.g., processing power and memory) of the medical system 10 and/or the granularity of ABRP feature vectors needed to reliably monitor patients.

The processing and generation of the ABRP feature vectors are suitably performed in parallel with, and independent of, the processing and generation of the PPG feature vectors. Further, the ASPU 40 and/or AFEU 42 can each be software (i.e., processor executable instructions), hardware, or a combination of the two. When the ASPU 40 or the AFEU 42 is, or includes, software, the software is stored on one or more program memories and executed by one or more processors.

An ABRP device 44 is positioned proximate to the patient 14, typically at the patient's bedside. Further, the ABRP device 44 can be integrated with the ABRP probe 36 and/or the PPG device 20. The ABRP device 44 controls the ABRP probe 36 and receives the acceleration signals generated by the ABRP probe 36. The ABRP device 44 includes the ASPU 40 and typically the AFEU 42. However, the ASPU 40 can be remote from the ABRP device 44, for example, within a PMS.

Using the ASPU 40, the ABRP device 44 processes the accelerometer signals to generate the pulse, respiration, position and activity signals. Where the ABRP device 44 includes the AFEU 42, the ABRP device 44 uses the AFEU 42 to process the signals and generate the ABRP feature vectors. The ABRP feature vectors are then relayed to the PMS 22 as they are generated using a communication unit 46 of the ABRP device 44. Where the ABRP device 44 does not include the AFEU 42, the ABRP device 44 relays the signals to the AFEU 18 using the communication unit 46.

One or more program memories 48 of the ABRP device 44 store any software of the ASPU 40 and/or the AFEU 42. Further, one or more processors 50 of the ABRP device 44 execute the software on the program memories 48. One or more system buses 52 interconnect the components of the ABRP device 44, such as the processors 50, the program memories 48 and the communication unit 46.

As illustrated in FIG. 1, both the ASPU 40 and the AFEU 42 are software stored on the program memories 48 of the ABRP device 44, where the processors 50 of the ABRP device 44 execute the software. As illustrated in FIG. 2, both the ASPU 40 and the AFEU 42 are software. The ASPU 40 is stored on the program memories 48 of the ABRP device 44, where the processors 50 of the ABRP device 44 execute the software. Further, the AFEU 42 is stored on the program memories 32 of the PMS 22, where the processors 34 of the PMS 22 execute the software.

An arrhythmia unit 54 of the PMS 22 receives or generates the PPG feature vectors and the ABRP feature vectors from the PFEU 18 and the AFEU 42, respectively. Based on the feature vectors, the arrhythmia unit 54 detects arrhythmic events, such as Atrial Fibrillation or Flutter (A-Fib), Ventricular Tachycardia (V-Tach), Ventricular Fibrillation (V-Fib), and Asystole. The arrhythmia unit 54 can be software (i.e., processor executable instructions), hardware, or a combination of the two.

When PPG feature vectors, ABRP pulse feature vectors, and ABRP respiration feature vectors temporally corresponding to the ABRP pulse feature vectors are received, the arrhythmia unit 54 employs a segment alignment routine to align the PPG feature vectors with the ABRP feature vectors. Notably, the ABRP respiration feature vectors and the ABRP pulse feature vectors are already aligned since these feature vectors are generated from the same time window or derived from data collected and transmitted on the same period.

The segment alignment routine aligns the PPG feature vectors with the ABRP feature vectors by aligning the pulses of the PPG feature vectors to the pulses of the ABRP pulse feature vectors. Alternatively, the ABRP pulse feature vectors can also be aligned to the PPG feature vectors. However, this would require the additional action of aligning the ABRP respiration feature vectors. Hence, for ease of discussion, it is assumed that the PPG feature vectors are aligned to the ABRP feature vectors.

One approach for aligning the features vectors is to employ trend analysis of the IBIs. In such a case, the trend of the IBIs of the PPG feature vectors are aligned to the trend of the IBIs of the ABRP pulse feature vectors. If the trends can be aligned, the pulse references of the PPG feature vectors are shifted so the pulse references of pulses in the PPG feature vectors match the pulse references of the corresponding pulses in the ABRP pulse feature vectors. Other approaches to aligning the PPG feature vector with the ABRP feature vectors are equally amenable.

After performing the segment alignment routine, a determination is made as to whether the PPG feature vectors are aligned with the ABRP feature vectors. This determination is typically based on the IBIs and performed in case the segment alignment routine isn't able to align the PPG feature vectors and the ABRP feature vectors. Insofar as this is the case, the arrhythmia unit 54 waits for additional data. Further, a user of the medical system 10 can be prompted, using, for example, a display device 56 of the PMS 22 or a message initiated by the PMS 22 to the user, to verify the ABRP feature vectors and PPG feature vectors are from the same patient. Otherwise, the arrhythmia unit 54 evaluates the ABRP feature vectors and the PPG feature vector for arrhythmic events. This includes identifying patterns indicative of arrhythmic events.

The onset of A-Fib is detected if the trend of the IPI goes from regular to persistently irregularly irregular and the activity level is below a predetermined threshold. The predetermined threshold is set by a user of the medical system at levels deemed sufficiently indicative of the onset of A-Fib. Similarly, the end of A-Fib is detected if the trend of IPI goes from irregularly irregular to persistently regular and the activity level is below the predetermined threshold. Tachyarrhythmia with hemodynamic compromise is detected if the IPI becomes regular, fast, and persistent AND the activity level is below the predetermined threshold and PPG signal amplitude drops.

If any of the foregoing events are detected, clinicians can be prompted, for example, by way of the display device 56 to check for the detected event. Further, if any of the foregoing events are detected and either position indicates a fall or the activity level acutely decreases in activity, the event is deemed more severe. In this case, an alert can be provided to clinicians, for example, by way of the display device 56 or alternative wireless messaging methods, such as e-mail, text, short messaging service (SMS), audio, suitable haptic devices, etc.

When the PMS 22 includes software, from, for example, the arrhythmia unit 54, the AFEU 42, or the PFEU 18, the PMS 22 includes one or more program memories 32 storing the software and one or more processors 34 executing the software. Further, communication with remote devices and/or systems, such as devices and/or systems including the PFEU 18 or AFEU 42, is suitably performed over a communication network using a communication unit 58 of the PMS 22. The components of the PMS 22 are suitably interconnected by way of a system bus 60 and/or a communication network.

Figure 3:
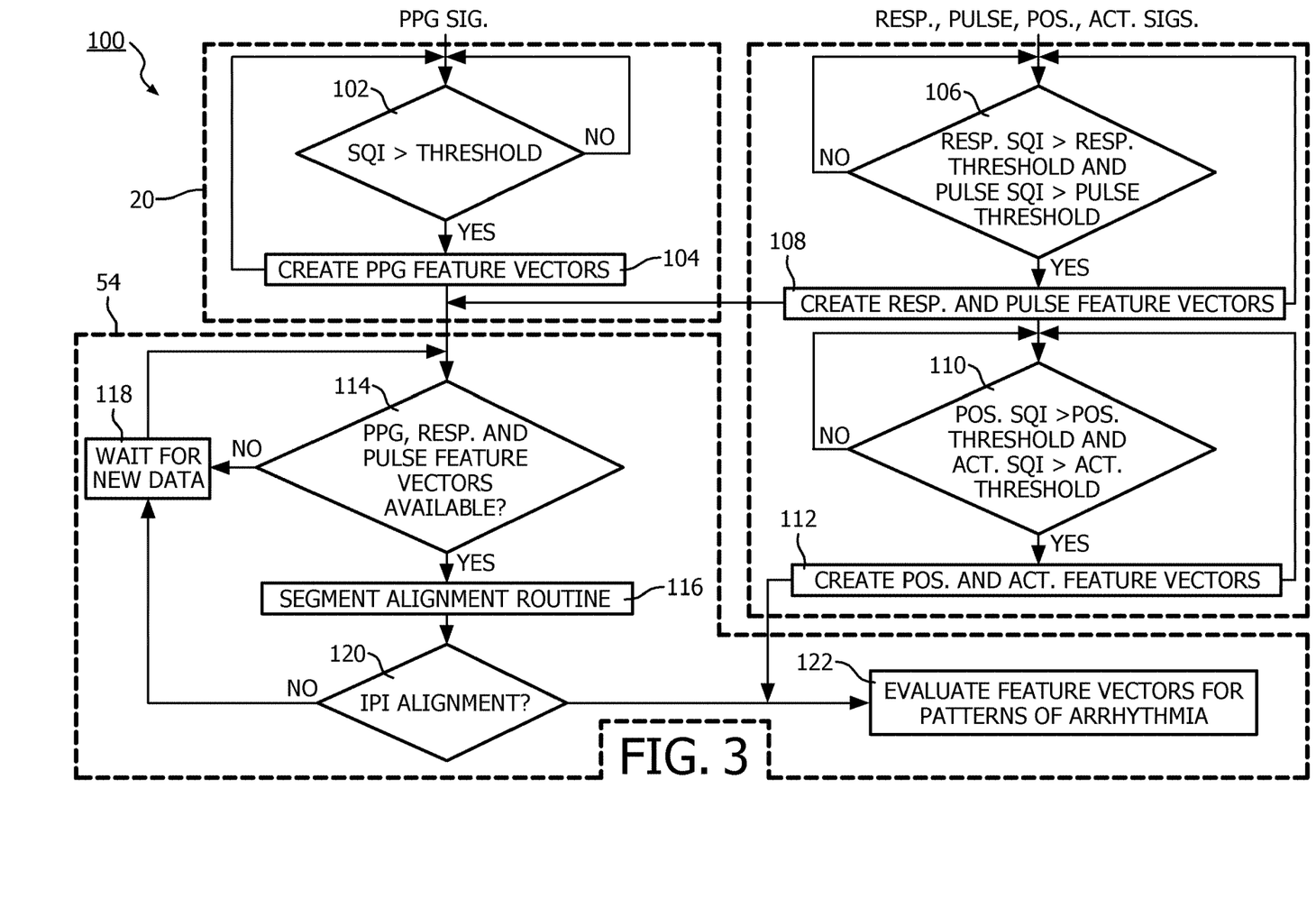
FIG. 3 illustrates a flow chart for detecting arrhythmic events with the systems of FIG. 1 or 2.

With reference to FIG. 3, a flow chart 100 illustrates how the PFEU 18, AFEU 42 and arrhythmia unit 54 coordinate to detect arrhythmic events. The PFEU 18 receives the PPG signal from, for example, the PSPU 16. Typically, the PPG signal is continuous. The PFEU 18 determines 102 whether the SQI exceeds a threshold. If the SQI does not exceed the threshold, the determination 102 is repeated, optionally after a delay. If the SQI exceeds the threshold, PPG feature vectors are created 104 from the PPG signal and the determination 102 is repeated, optionally after a delay.

The AFEU 42 operates in parallel with, and independent of, the PFEU 18 and receives respiration, pulse, position and activity signals from, for example, the ASPU 40. Typically, the signals are continuous. The AFEU 42 determines 106 whether the SQIs of these signals both exceed corresponding thresholds. If the SQIs do not both exceed corresponding thresholds, the determination 106 is repeated, optionally after a delay. If the SQIs both exceed corresponding thresholds, ABRP respiration and pulse feature vectors are created 108 from the pulse and respiration signals and the determination 106 is repeated, optionally after a delay.

Further, after creating ABRP respiration and pulse feature vectors, the AFEU 42 determines 110 whether the SQIs of these signals both exceed corresponding thresholds. If the SQIs do not both exceed corresponding thresholds, the determination 110 is repeated, optionally after a delay. If the SQIs both exceed corresponding threshold, ABRP position and activity feature vectors are created 112 from the position and activity signals and the determination 110 is repeated, optionally after a delay.

The arrhythmia unit 54 receives PPG feature vectors, as well as ABRP respiration and pulse feature vectors, from the PFEU 18 and the AFEU 42. When it is determined 114 that both PPG feature vectors and ABRP respiration and pulse feature vectors are available, a segment alignment routine is performed 116 to attempt to align the PPG feature vectors to the ABRP respiration and pulse feature vectors, or vice versa. Otherwise, the determination 114 is repeated after waiting for new data 118. Suitably, alignment is performed based on IPIs.

After performing 116 the segment alignment routine, a determination 120 is made as to whether the IPIs of the PPG feature vectors are aligned to the ABRP respiration and pulse feature vectors. If not aligned, the determination 114 of availability is repeated after waiting 118 for new data. If aligned, the PPG feature vectors and the ABRP respiration, pulse, position and activity feature vectors are evaluated 122 for patterns of arrhythmia. For example, the onset of A-Fib is detected if the trend of the IPI goes from regular to persistently irregular AND the activity level is below a predetermined threshold.

Although memories 26, 32 and 48 are shown as separate memories for ease of explanation, in some embodiments two or all of these memories are embodied in a single memory. Similarly, although processors 28, 34, 50 are shown as separate processors for ease of explanation, in some embodiments two or all of these processors are embodied in a single processor. Even more, messages, alerts, and the like which have been described above can be conveyed to users by way of display devices or alternative wireless messaging methods, such as e-mail, text, short messaging service (SMS), audio, suitable haptic devices, etc.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes: 1) at least one memory with processor executable instructions to perform the functionality of the controller; and 2) at least one processor executing the processor executable instructions; a user output device includes a printer, a display device, and the like; and a display device includes one or more of a liquid crystal display (LCD), an light-emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical system for detecting arrhythmic events, said system comprising:
at least one processor programmed to:
receive a photoplethysmogram (PPG) signal generated using a PPG probe positioned on or within a patient;
receive a pulse signal generated using an accelerometer positioned on or within the patient;
extract features from the PPG signal to generate PPG feature vectors;
extract features from the pulse signal to generate pulse feature vectors;
correlate the PPG feature vectors with the pulse feature vectors; and
evaluate correlated PPG feature vectors and correlated pulse feature vectors to detect arrhythmic events;
wherein features extracted from the PPG signal include inter pulse intervals (IPIs) for pairs of adjacent pulses of a last predetermined number of pulses; and
wherein features extracted from the pulse signal include inter pulse intervals (IPIs) for pairs of adjacent pulses of a last predetermined number of pulses.

2. The medical system according to claim 1, wherein the at least one processor is further programmed to:
receive a respiration signal generated using the accelerometer positioned on or within the patient;
extract features from the respiration signal to generate respiration feature vectors;

correlate the PPG feature vectors with the respiration feature vectors; and evaluate correlated respiration feature vectors to detect arrhythmic events.

3. The medical system according to claim 2, wherein the at least one processor is further programmed to: extract features from the pulse and respiration signals when both a signal quality index (SQI) of the pulse signal exceeds a predetermined threshold and an SQI of the respiration signal exceeds a predetermined threshold.

4. The medical system according to claim 1, wherein correlating the PPG feature vectors with the pulse feature vectors includes:

aligning inter pulse interval (IPI) trends of the pulse feature vectors with IPI trends of the PPG feature vectors.

5. The medical system according to claim 1, wherein the at least one processor is further programmed to:

receive a position signal, and an activity signal, generated using the accelerometer; and extract features from the position and activity signals to generate position feature vectors and activity feature vectors, respectively, wherein evaluating the correlated PPG feature vectors and the correlated pulse feature vectors to detect the arrhythmic events uses the position and activity feature vectors.

6. The medical system according to claim 1, wherein features are extracted from the PPG signal in parallel with, and independent of, extraction of features from the pulse signal.

7. The medical system according to claim 1, wherein:

the at least one processor is further programmed to receive an activity signal generated using the accelerometer, wherein the activity signal indicates an activity level; and evaluating the correlated PPG feature vectors and the correlated pulse feature vectors to detect the arrhythmic events includes at least one of:

detecting onset of atrial fibrillation or flutter (A-Fib) in response to inter pulse interval (IPI) trend going from regular to persistently irregularly irregular and the activity level being below a predetermined threshold;

detecting end of the A-Fib in response to IPI trend going from irregularly irregular to persistently regular and the activity level being below the predetermined threshold; and detecting tachyarrhythmia with hemodynamic compromise in response to IPI becoming regular, fast, and persistent and the activity level being below the predetermined threshold and PPG signal amplitude dropping.

8. The medical system according to claim 1, further including a photoplethysmogram (PPG) device generating the PPG signal using the PPG probe positioned on or within the patient; and an accelerometer based respiration and pulse (ABRP) device generating the pulse signal using the accelerometer positioned on or within the patient.

9. The medical system according to claim 1, wherein:

the at least one processor is further programmed to receive an activity signal generated using the accelerometer, wherein the activity signal indicates an activity level; and evaluating the correlated PPG feature vectors and the correlated pulse feature vectors to detect the arrhythmic events includes:

detecting tachyarrhythmia with hemodynamic compromise in response to IPI becoming regular, fast, and persistent and the activity level being below the predetermined threshold and PPG signal amplitude dropping.

10. A medical method, performed by one or more processors, for detecting arrhythmic events, said method comprising:

receiving a photoplethysmogram (PPG) signal generated using a PPG probe positioned on or within a patient;

receiving a pulse signal generated using an accelerometer positioned on or within the patient;

extracting features from the PPG signal to generate PPG feature vectors;

extracting features from the pulse signal to generate pulse feature vectors;

correlating the PPG feature vectors with the pulse feature vectors; and, evaluating correlated PPG feature vectors and correlated pulse feature vectors to detect arrhythmic events;

wherein features extracted from the PPG signal include inter pulse intervals (IPIs) for pairs of adjacent pulses of a last predetermined number of pulses;

wherein features extracted from the pulse signal include inter pulse intervals (IPIs) for pairs of adjacent pulses of a last predetermined number of pulses; and wherein the evaluating of the correlated PPG feature vectors and correlated pulse feature vectors to detect arrhythmic events does not use electrocardiograph (ECG) data.

11. The medical method according to claim 10, further including:

receiving a respiration signal generated using the accelerometer positioned on or within the patient;

extracting features from the respiration signal to generate respiration feature vectors;

correlating the PPG feature vectors with the respiration feature vectors; and evaluating correlated respiration feature vectors to detect arrhythmic events.

12. The medical method according to claim 11, further including:

detecting that both a signal quality index (SQI) of the pulse signal exceeds a predetermined threshold and an SQI of the respiration signal exceeds a predetermined threshold; and in response to the detection, extracting features from the pulse and respiration signals.

13. The medical method according to claim 10, wherein correlating the PPG feature vectors with the pulse feature vectors includes:

aligning inter pulse interval (IPI) trends of the ABRP pulse feature vectors with IPI trends of the PPG feature vectors.

14. The medical method according to claim 10, further including:

receiving a position signal, and an activity signal, generated using the accelerometer;

extracting features from the position and activity signals to generate position feature vectors and activity feature vectors, respectively; and evaluating the correlated PPG feature vectors and the correlated pulse feature vectors to detect the arrhythmic events using the position and activity feature vectors.

15. The medical method according to claim 10, wherein features are extracted from the PPG signal in parallel with, and independent of, extraction of features from the pulse signal.

16. The medical method according to claim 10, wherein:
the method further includes receiving an activity signal generated using the accelerometer, wherein the activity signal indicates an activity level; and
evaluating the correlated PPG feature vectors and the correlated pulse feature vectors to detect the arrhythmic events includes at least one of:
detecting end of atrial fibrillation (A-Fib) in response to inter pulse interval (IPI) trend going from irregularly irregular to persistently regular and the activity level being below the predetermined threshold; and
detecting tachyarrhythmia with hemodynamic compromise in response to IPI becoming regular, fast, and persistent and the activity level being below the predetermined threshold and PPG signal amplitude dropping.

17. The medical method according to claim 10, further comprising:
based on a detected arrhythmic event, prompting a user to check for the detected arrhythmic event.

18. The medical method according to claim 10, further comprising:
based on a detected arrhythmic event, providing an alert on a display device.

19. The medical method according to claim 10, further comprising:
with the PPG probe, generating the PPG signal.

20. A non-transitory computer readable medium carrying software which contains one or more processors to perform the method according to claim 10.

21. A medical system for detecting arrhythmic events, said system comprising:
at least one processor programmed to:
receive a photoplethysmogram (PPG) signal generated using a PPG probe positioned on or within a patient;
receive a pulse signal generated using an accelerometer positioned on or within the patient;
extract features from the PPG signal to generate PPG feature vectors;
extract features from the pulse signal to generate pulse feature vectors;
correlate the PPG feature vectors with the pulse feature vectors; and
evaluate correlated PPG feature vectors and correlated pulse feature vectors to detect arrhythmic events;
wherein features extracted from the PPG signal include inter pulse intervals (IPIs) for pairs of adjacent pulses of a last predetermined number of pulses;
wherein features extracted from the pulse signal include inter pulse intervals (IPIs) for pairs of adjacent pulses of a last predetermined number of pulses; and
wherein the at least one processor is further programmed to:
extract the features from the PPG signal according to a predetermined sampling rate, the predetermined sampling rate set based upon computational resources of the medical system, the computational resources including a processing power and a memory.

* * * * *